United States Patent [19]

Bennett

[11] Patent Number: Plant 6,455

[45] Date of Patent: Dec. 13, 1988

[54] MINIATURE ROSE PLANT 'FAT 'N SASSY'

[76] Inventor: Cecilia L. D. Bennett, 489 Minot Ave., Chula Vista, Calif. 92010

[21] Appl. No.: 10,720

[22] Filed: Feb. 4, 1987

[51] Int. Cl.[4] ..... A01H 5/00

[52] U.S. Cl. ..... Plt./7

[58] Field of Search ..... Plt./7

*Primary Examiner*—James R. Feyrer

[57] ABSTRACT

The subject of the present disclosure is a new and distinct variety of miniature rose plant, named 'Fat 'N Sassy', which is characterized by its pale yellow to near white blooms with a blush of red, ranging from near Crimson to near Tyrian Rose, that covers all sun-exposed surfaces. The hybrid tea form miniature rose is larger than the average miniature in bloom size and usually borne one to a stem or on occasion in sprays of 3 to 5 or more. The bush is vigorous, upright, bushy and produces moderate to heavy quantities of bloom.

1 Drawing Sheet

1

The present invention relates to a new and distinct variety or a hardy, dwarf, bush plant to the miniature class; the variety being primarily characterized as a red blend.

The variety is further characterized by:

Long stemmed blooms of hybrid tea-type form, borne usually one to a stem but on occasion in sprays of 3 to 5 or more. The blooms are held very erect and well above the foilage.

It has a slight fragrance.

The plant ranges in height from 24 to 36 inches (approximately 60 to 90 cm). The canes are sturdy and erect with moderate branching and medium to heavy foilage covering. The plant is a moderate to heavy bloomer that does well either in the greenhouse or outdoors.

The plant has good growth habits, well-shaped and attractive, bearing numerous leaflets of average to slightly large size for a miniature rose.

The seed parent was Carrousel (U.S. Plant Pat. No. 1,066), and the pollen parent was Sheri Anne (U.S. Plant Pat. No. 3,826). It differs from its seed parent in the following ways. It is a miniature of the red blend class, and Carrousel is a grandiflora of the medium red class. It differs from its pollen parent in the following ways. It is larger than average bloom for a miniature (40 to 60 mm in diameter) of the red blend class, and Sheri Anne is an average size miniature (30 to 40 mm in diameter) of the orange-red class.

The descriptive matter which follows, pertains to roses grown and color values observed in plants and newly opened blooms in the months of March through August 1986. The plants were grown outdoors in Chula Vista, Calif., and are believed to be accurate standards for this cultivar in similar conditions of soil and climate elsewhere.

The color photograph illustrates the variety.

Referring now specially to the new and distinct variety of miniature rose plant named 'Fat 'N Sassy', the following is a detailed description thereof in outline; all major color plate identifications being by reference to the British Colour Council Horticultural Colour Chart, except where common terms of color definition are employed.

Type: Hardy, dwarf, bushy, greenhouse or outdoor, exhibition quality or garden decorative potted plant.

2

Class: Miniature.

Variety name: Fat 'N Sassy.

Flowers borne: Usually one to a stem, but occasionally in sprays of 3 to 5 or more on erect stems with foliage well below the blooms.

Quantity of bloom: Moderate to heavy both outdoors or greenhouse grown.

Bud:

*Peduncle.*—Average length (35 to 45 mm); average diameter and sturdy; ranging from near Scheeles Green (860/3 to 860/1 page 860) to near Lettuce Green (861/3 to 861/1 page 861) with occasional tinting of bronze.

*Hairs.*—Extremely small and numerous with a reddish color; located over the entire surface of the peduncle and sepals, but not present on the calyx tube.

*Calyx.*—Same color as the peduncle and without hairs.

*Opening.*—Opens well in all weather.

Bloom:

*Size when fully open.*—Slightly larger than average for a miniature variety (40 to 60 mm).

*Petalage.*—Double — Averaging about 25 to 30 petals, arranged regularly, plus petaloids (10 to 20 or more).

*Form.*—Urnshaped to ovoid as the bloom progresses. The petals remain at first somewhat tightly cupped with the tips and/or margins reflexed outward, becoming at maturity more loosely cupped.

Petals: Fairly thick with good substance; both the upper and under surfaces of all petals have a matte finish.

Shape.—Outer petal and intermediate petals are of a broad obovate form. The inner petals are a broad lanceolate form; and the petaloids are also lanceolate form with some occasional irregularities.

Color: Newly opened flowers from plants grown outdoors (March through August 1986), Chula Vista, Calif.

*All petals.*—Upper surface — Ranging from near Mimosa Yellow (602/3 to 602/2 page 602) to near white as the bloom opens with a blush on the outer margin, ranging from near Crimson (22/2 to 22 page 22) to near Tyrian Rose (24/2 to 24 page 24), which spreads across the petals to all sun-exposed surfaces of the blooms. Under Surface — Ranging from near Mimosa Yellow (602/3 to 602/2 page 602) to near white as the bloom opens with a blush on the outer margin, ranging from near Crimson (22/2 to 22/1 page 22) to near Carmine Rose (621/1 to 621 page 621).

*General color effect.*—Newly opened flowers — Pale yellow to near white with a deep rose to red blush on the outer margin of all petals. Three days open — No yellow tones present; all sun-exposed surfaces are deep rose to red with near white on the unexposed areas of the upper surface and the base of all under surfaces.

*Flower longevity.*—(March through August 1986) Plant in pot 4 to 7 days from bud with sepals reflexed to fully opened bloom. Holding at fully opened with increased deepening of the red tones over all sun-exposed surfaces for 5 to 7 days or longer. Cut blooms at living room temperature 6 to 8 days or longer.

Reproductive organs:

*Stamens.*—A generous amount arranged uniformly around the pistil.

*Filaments.*—Varying in length with shorter filaments more proximal to the pistil; pale yellow in color with golden yellow anthers.

*Pollen.*—Abundant.

*Pistil.*—Long, abundant and spreading; pale yellow at the base to reddish at the top with pale yellow caps on the styles.

*Ovaries.*—All encased in calyx.

*Hips.*—Some.

*Seed.*—3 to 5 in each hip.

*Sepals.*—Permanent; spear-shaped; open as the bloom opens, but does not recurve against the peduncle.

Foliage:

*Leaves.*—Five to seven leaflets on the average; average to slightly larger than average for a miniature rose plant.

*Leaflets.*—Broad ovate-shaped.

*Margin.*—Very serrated with occasional tinting of bronze, especially noticeable on the newer foliage.

*Color.*—Near Spinach Green (0960/2 to 0960 page 0960) with occasional bronzing of the margins, especially noticeable on the newer foliage. The upper surfaces have a semi-glossy finish, and the under surfaces have a matte finish of a slightly lighter shade than the upper surfaces.

*Rachis.*—Medium strength; upper surface is grooved with very small hairs over the length of it. Under surface has few if any hairs but does contain 3 to 5 small thorns.

*Stipules.*—Varying in length from small to medium; average width; tapering auricles angled outward at about 45 degrees.

Growth:

*Habit.*—Dwarf, bushy; average to tall height for a miniature rose plant.

*Growth.*—Upright and vigorous.

*Canes.*—Medium diameter; sturdy; held erect.

*Main Stems.*—Same color as the foliage.

*Thorns.*—Averaging 12 to 15 per 10 cm on the main stems and fewer on the branches. Reddish in color with occasional tinting of bronze. Small to average in size. Slender and hooked slightly downward.

*Branches.*—Same color as the foliage.

The miniature rose plant and its flowers as herein described may vary in slight detail due to climate, soil and cultural conditions under which the variety may be grown; the present description being of the variety as grown at Chula Vista, Calif.

I have found this variety to be easily asexually reproduced from cuttings.

The following is claimed:

1. A new and distinct variety of miniature rose plant named 'Fat 'N Sassy' of hardy, dwarf, vigorous growth, well-branched and attractive appearance, substantially as illustrated and described, characterized by its blooms of pale yellow to near white with a blush of red, ranging from near Crimson to near Tyrian Rose, that covers all sun-exposed surfaces.

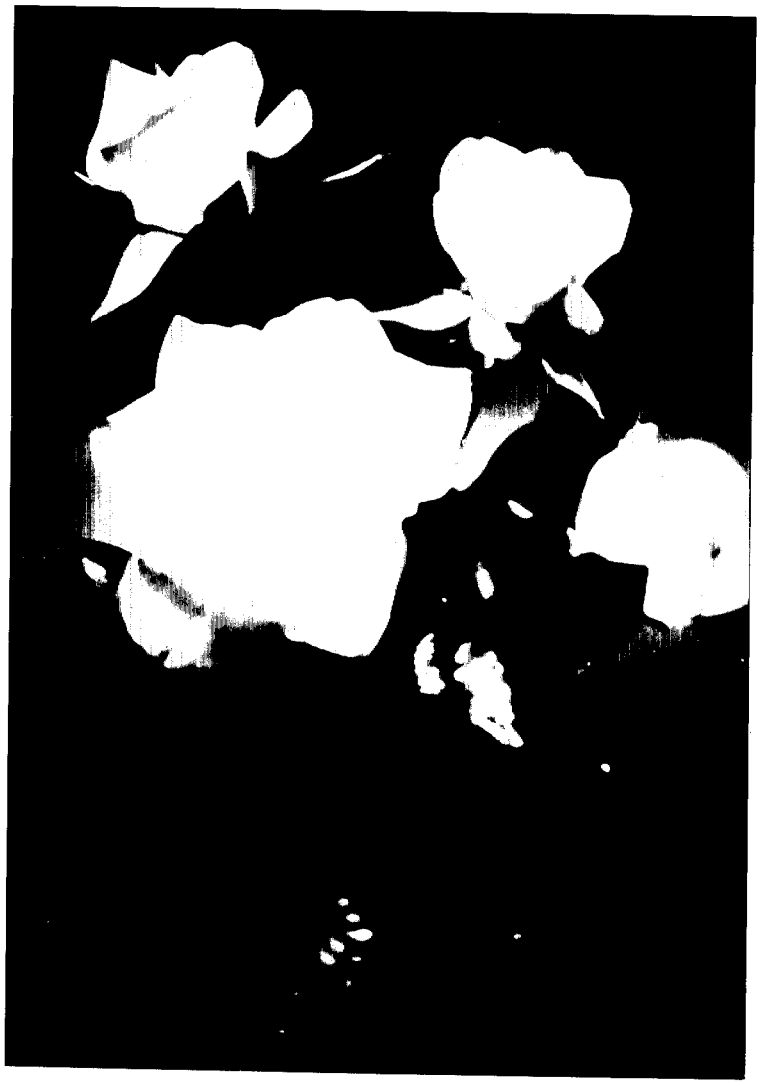

* * * * *